United States Patent
Jin et al.

(10) Patent No.: US 10,023,881 B2
(45) Date of Patent: Jul. 17, 2018

(54) DETOXIFYING PRE-TREATED LIGNOCELLULOSE-CONTAINING MATERIALS

(75) Inventors: Qiming Jin, Sacremento, CA (US); Jiyin Liu, Raleigh, NC (US); Bjorn Lennart Pierre Alexander Cassland, Malmo (SE); Donald L. Higgins, Franklinton, NC (US)

(73) Assignees: NOVOZYMES A/S, Bagsvaerd (DK); NOVOZYMES NORTH AMERICA, INC., Franklinton, NC (US); NOVOZYMES INC., Davis, CA (US)

( * ) Notice: Subject to any disclaimer, the term of this patent is extended or adjusted under 35 U.S.C. 154(b) by 198 days.

(21) Appl. No.: 12/597,834

(22) PCT Filed: Apr. 18, 2008

(86) PCT No.: PCT/US2008/060766
§ 371 (c)(1),
(2), (4) Date: Nov. 24, 2009

(87) PCT Pub. No.: WO2008/134259
PCT Pub. Date: Nov. 6, 2008

(65) Prior Publication Data
US 2010/0273227 A1      Oct. 28, 2010

Related U.S. Application Data

(60) Provisional application No. 60/913,581, filed on Apr. 24, 2007, provisional application No. 60/946,272, filed on Jun. 26, 2007, provisional application No. 60/988,949, filed on Nov. 19, 2007.

(51) Int. Cl.
*C12P 7/10*           (2006.01)

(52) U.S. Cl.
CPC ............... *C12P 7/10* (2013.01); *Y02E 50/16* (2013.01)

(58) Field of Classification Search
None
See application file for complete search history.

(56) References Cited

U.S. PATENT DOCUMENTS

2004/0253696 A1* 12/2004 Grichko ................. 435/161
2006/0005279 A1*  1/2006 Dotson et al. ........... 800/284

FOREIGN PATENT DOCUMENTS

WO      2005/074656 A2    8/2005
WO        2006110900 A2   10/2006
WO    WO 2008/085356      7/2008

OTHER PUBLICATIONS

Berson et al., Applied Biochemistry and Biotechnology, 2006, vol. 129-132, p. 612-620.*
Sun et al., Bioresource Technology, 2002, vol. 83, p. 1-11.*
Liu et al., Applied Biochemistry and Biotechnology, 2005, vol. 121-124, p. 451-460.*
Stenberg et al., J. Chem. Technol. Biotechnol., 1998, vol. 71, p. 299-308.*
Larsson et al., Applied and Environmental Microbiology, 2001, vol. 67, No. 3, p. 1163-1170.*
Palmquist et al. "Fermentation of Lignocellulosic Hydrolysates 1: Inhibition and Dextoxification" BioResource Technology, vol. 74, No. 1, pp. 17-24 (2000).
Larsson et al. "Development of a *Saccharomyces cerevisiae* strain with enhanced resistance to phenolic fermentation inhibitors in lignocellulose hydrolysates by heterologous expression of 1 acC3IS6" Applied and Environmental Microbiology, vol. 67, No. 3, pp. 1163-1170 (2001).
Larsson et al., "Methods for the Detoxification of Lignocellulose Hydrolyzates of Spruce" Applied Biochemistry and Biotechnology, vol. 77-79, pp. 91-103 (1999).
Jonsson et al., "Detoxification of Wood Hydrolysates with Laccase and Peroxidase from the White-Rot Fungus Trametes Versicolor" Applied Microbiology and Biotechnology, vol. 49, No. 6, pp. 691-697 (1998).
Chandel et al., "Detoxification of sugarcane bagasse hydrolysate improves ethanol production by Candida shehatae NCIM 3501", Bioresource Technology, vol. 98, pp. 1947-1950 (2007).
Hetti Palonen, VTT Publications 520 pp. 1-8 (2004).
Palonen et al., Biotechnology and Bioengineering, vol. 86, No. 5, pp. 550-557 (2004).
Tabka et al., Enzyme and Microbial Technology, vol. 39, pp. 897-902 (2006).
Tian et al, 2006, Transactions of the CSAE 22, 221-224.
Palmqvist et al, 1997, Enzyme Microb Technol, vol. 20, pp. 286-293.

* cited by examiner

*Primary Examiner* — Kade Ariani
(74) *Attorney, Agent, or Firm* — Joshua Price

(57) ABSTRACT

The invention relates to a process of detoxifying pre-treated lignocellulose-containing material comprising subjecting the pre-treated lignocellulose-containing material to one or more phenolic compound oxidizing enzymes.

5 Claims, 1 Drawing Sheet

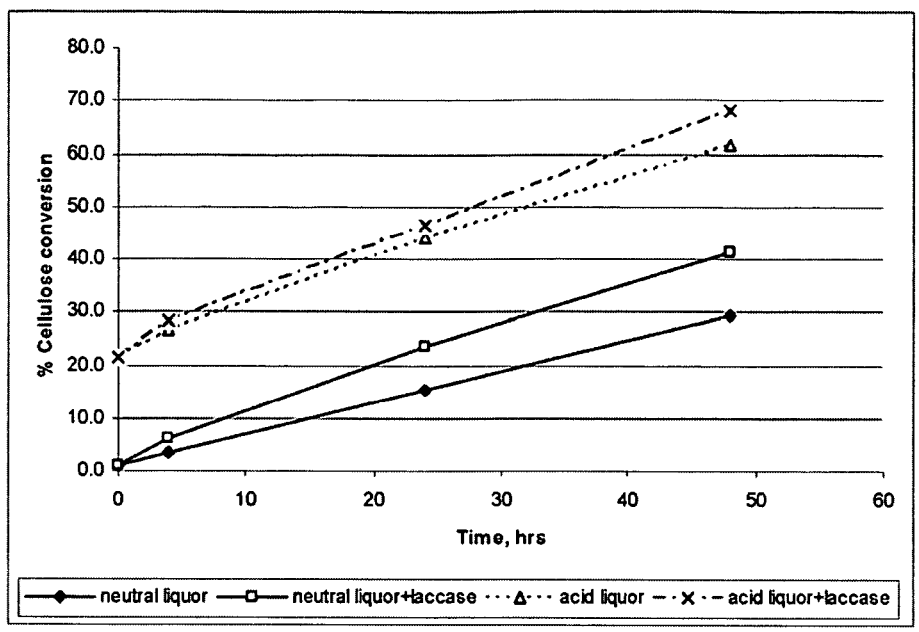

SEQUENCE LISTING

```
<160> NUMBER OF SEQ ID NOS: 13

<210> SEQ ID NO 1
<211> LENGTH: 483
<212> TYPE: PRT
<213> ORGANISM: B. licheniformis

<400> SEQUENCE: 1

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140
```

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Asn Glu Asn Gly Asn
        180                 185                 190

Tyr Asp Tyr Leu Met Tyr Ala Asp Ile Asp Tyr Asp His Pro Asp Val
    195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
        260                 265                 270

Tyr Leu Asn Lys Thr Asn Phe Asn His Ser Val Phe Asp Val Pro Leu
    275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
        340                 345                 350

Thr Arg Glu Ser Gly Tyr Pro Gln Val Phe Tyr Gly Asp Met Tyr Gly
    355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
        420                 425                 430

Gly Gly Ala Lys Arg Met Tyr Val Gly Arg Gln Asn Ala Gly Glu Thr
    435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 2
<211> LENGTH: 480
<212> TYPE: PRT
<213> ORGANISM: B. amyloliquefaciens

<400> SEQUENCE: 2

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

-continued

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
 50                  55                  60

Phe Gln Gln Lys Gly Thr Val Arg Thr Lys Tyr Gly Thr Lys Ser Glu
 65                  70                  75                  80

Leu Gln Asp Ala Ile Gly Ser Leu His Ser Arg Asn Val Gln Val Tyr
                 85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
            130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
            210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
                260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Gly Tyr Asp Met
            290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Thr Ser Pro Lys Glu Ile Pro Ser Leu Lys Asp Asn Ile
            370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser

```
                    450                 455                 460
Asp Gly Trp Gly Glu Phe His Val Asn Asp Gly Ser Val Ser Ile Tyr
465                 470                 475                 480

<210> SEQ ID NO 3
<211> LENGTH: 514
<212> TYPE: PRT
<213> ORGANISM: B. stearothermophilus

<400> SEQUENCE: 3

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350
```

```
Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205
```

```
Asp His Pro Glu Val Ile His Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 5
<211> LENGTH: 485
<212> TYPE: PRT
<213> ORGANISM: Bacillus sp.

<400> SEQUENCE: 5

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95
```

Val Gln Val Tyr Gly Asp Val Met Asn His Lys Gly Gly Ala Asp
            100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
            130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
            210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 6
<211> LENGTH: 478

```
<212> TYPE: PRT
<213> ORGANISM: Artificial Sequence
<220> FEATURE:
<223> OTHER INFORMATION: Synthetic construct

<400> SEQUENCE: 6

Ala Thr Pro Ala Asp Trp Arg Ser Gln Ser Ile Tyr Phe Leu Leu Thr
  1               5                  10                  15

Asp Arg Phe Ala Arg Thr Asp Gly Ser Thr Thr Ala Thr Cys Asn Thr
             20                  25                  30

Ala Asp Gln Lys Tyr Cys Gly Gly Thr Trp Gln Gly Ile Ile Asp Lys
         35                  40                  45

Leu Asp Tyr Ile Gln Gly Met Gly Phe Thr Ala Ile Trp Ile Thr Pro
 50                  55                  60

Val Thr Ala Gln Leu Pro Gln Thr Thr Ala Tyr Gly Asp Ala Tyr His
 65                  70                  75                  80

Gly Tyr Trp Gln Gln Asp Ile Tyr Ser Leu Asn Glu Asn Tyr Gly Thr
                 85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Glu Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
        355                 360                 365

Arg Asn Tyr Ala Ile Ser Lys Asp Thr Gly Phe Val Thr Tyr Lys Asn
    370                 375                 380
```

Trp Pro Ile Tyr Lys Asp Asp Ile Thr Ile Ala Met Arg Lys Gly Thr
385                 390                 395                 400

Asp Gly Ser Gln Ile Val Thr Ile Leu Ser Asn Lys Gly Ala Ser Gly
            405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Gly Ser Asp
        435                 440                 445

Gly Asn Val Pro Val Pro Met Ala Gly Gly Leu Pro Arg Val Leu Tyr
    450                 455                 460

Pro Thr Glu Lys Leu Ala Gly Ser Lys Ile Cys Ser Ser Ser
465                 470                 475

<210> SEQ ID NO 7
<211> LENGTH: 586
<212> TYPE: PRT
<213> ORGANISM: Artificial Sequence
<220> FEATURE:
<223> OTHER INFORMATION: Synthetic construct

<400> SEQUENCE: 7

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Pro
        115                 120                 125

Gly Ser Ser Val Asp Tyr Ser Val Phe Val Pro Phe Asn Ser Ala Ser
    130                 135                 140

Tyr Phe His Pro Phe Cys Phe Ile Gln Asn Trp Asn Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Glu Val Leu Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

```
Tyr Asn Met Ile Asn Thr Val Lys Ser Asp Cys Pro Asp Ser Thr Leu
            275                 280                 285

Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320

Asn Asp Gly Ile Pro Ile Ile Tyr Ala Gly Gln Gln His Tyr Ala
                325                 330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
            355                 360                 365

Arg Asn Tyr Ala Ile Ser Lys Asp Thr Gly Phe Val Thr Tyr Lys Asn
    370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
            420                 425                 430

Gln Leu Thr Glu Val Ile Gly Cys Thr Thr Val Thr Val Asp Ser Ser
    435                 440                 445

Gly Asp Val Pro Val Pro Met Ala Gly Gly Leu Pro Arg Val Leu Tyr
            450                 455                 460

Pro Thr Glu Lys Leu Ala Gly Ser Lys Ile Cys Ser Ser Ser Gly Ala
465                 470                 475                 480

Thr Ser Pro Gly Gly Ser Ser Gly Ser Val Glu Val Thr Phe Asp Val
                485                 490                 495

Tyr Ala Thr Thr Val Tyr Gly Gln Asn Ile Tyr Ile Thr Gly Asp Val
            500                 505                 510

Ser Glu Leu Gly Asn Trp Thr Pro Ala Asn Gly Val Ala Leu Ser Ser
    515                 520                 525

Ala Asn Tyr Pro Thr Trp Ser Ala Thr Ile Ala Leu Pro Ala Asp Thr
530                 535                 540

Thr Ile Gln Tyr Lys Tyr Val Asn Ile Asp Gly Ser Thr Val Ile Trp
545                 550                 555                 560

Glu Asp Ala Ile Ser Asn Arg Glu Ile Thr Thr Pro Ala Ser Gly Thr
                565                 570                 575

Tyr Thr Gly Lys Asp Thr Trp Asp Glu Ser
            580                 585

<210> SEQ ID NO 8
<211> LENGTH: 558
<212> TYPE: PRT
<213> ORGANISM: Artificial Sequence
<220> FEATURE:
<223> OTHER INFORMATION: Rhizomucor pusillus amylase with linker and SBD
      from A. rolfsii

<400> SEQUENCE: 8

Ser Pro Leu Pro Gln Gln Gln Arg Tyr Gly Lys Arg Ala Thr Ser Asp
1               5                   10                  15

Asp Trp Lys Ser Lys Ala Ile Tyr Gln Leu Leu Thr Asp Arg Phe Gly
            20                  25                  30

Arg Ala Asp Asp Ser Thr Ser Asn Cys Ser Asn Leu Ser Asn Tyr Cys
        35                  40                  45
```

-continued

Gly Gly Thr Tyr Glu Gly Ile Thr Lys His Leu Asp Tyr Ile Ser Gly
       50                  55                  60

Met Gly Phe Asp Ala Ile Trp Ile Ser Pro Ile Pro Lys Asn Ser Asp
 65                  70                  75                  80

Gly Gly Tyr His Gly Tyr Trp Ala Thr Asp Phe Tyr Gln Leu Asn Ser
                 85                  90                  95

Asn Phe Gly Asp Glu Ser Gln Leu Lys Ala Leu Ile Gln Ala Ala His
             100                 105                 110

Glu Arg Asp Met Tyr Val Met Leu Asp Val Val Ala Asn His Ala Gly
         115                 120                 125

Pro Thr Ser Asn Gly Tyr Ser Gly Tyr Thr Phe Gly Asp Ala Ser Leu
     130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                 165                 170                 175

Asp Asn Val Ala Ile Leu Asn Asp Ile Val Ser Gly Trp Val Gly Asn
             180                 185                 190

Tyr Ser Phe Asp Gly Ile Arg Ile Asp Thr Val Lys His Ile Arg Lys
         195                 200                 205

Asp Phe Trp Thr Gly Tyr Ala Glu Ala Ala Gly Val Phe Ala Thr Gly
     210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                 245                 250                 255

Phe Val Ser Lys Ser Lys Gly Phe Ser Arg Ile Ser Glu Met Leu Gly
             260                 265                 270

Ser Asn Arg Asn Ala Phe Glu Asp Thr Ser Val Leu Thr Thr Phe Val
         275                 280                 285

Asp Asn His Asp Asn Pro Arg Phe Leu Asn Ser Gln Ser Asp Lys Ala
     290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                 325                 330                 335

Ala Asn Arg Glu Val Leu Trp Thr Thr Asn Tyr Asp Thr Ser Ser Asp
             340                 345                 350

Leu Tyr Gln Phe Ile Lys Thr Val Asn Ser Val Arg Met Lys Ser Asn
         355                 360                 365

Lys Ala Val Tyr Met Asp Ile Tyr Val Gly Asp Asn Ala Tyr Ala Phe
     370                 375                 380

Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
                 405                 410                 415

Ser Leu Met Asp Ile Val Ser Asn Ile Thr Thr Thr Val Ser Ser Asp
             420                 425                 430

Gly Thr Val Thr Phe Asn Leu Lys Asp Gly Leu Pro Ala Ile Phe Thr
         435                 440                 445

Ser Ala Gly Ala Thr Ser Pro Gly Gly Ser Ser Gly Val Glu Val
     450                 455                 460

```
Thr Phe Asp Val Tyr Ala Thr Thr Val Tyr Gly Gln Asn Ile Tyr Ile
465                 470                 475                 480

Thr Gly Asp Val Ser Glu Leu Gly Asn Trp Thr Pro Ala Asn Gly Val
                485                 490                 495

Ala Leu Ser Ser Ala Asn Tyr Pro Thr Trp Ser Ala Thr Ile Ala Leu
            500                 505                 510

Pro Ala Asp Thr Thr Ile Gln Tyr Lys Tyr Val Asn Ile Asp Gly Ser
            515                 520                 525

Thr Val Ile Trp Glu Asp Ala Ile Ser Asn Arg Glu Ile Thr Thr Pro
530                 535                 540

Ala Ser Gly Thr Tyr Thr Glu Lys Asp Thr Trp Asp Glu Ser
545                 550                 555
```

<210> SEQ ID NO 9
<211> LENGTH: 450
<212> TYPE: PRT
<213> ORGANISM: Rhizomucor pusillus

<400> SEQUENCE: 9

```
Ser Pro Leu Pro Gln Gln Gln Arg Tyr Gly Lys Arg Ala Thr Ser Asp
1               5                   10                  15

Asp Trp Lys Gly Lys Ala Ile Tyr Gln Leu Leu Thr Asp Arg Phe Gly
                20                  25                  30

Arg Ala Asp Asp Ser Thr Ser Asn Cys Ser Asn Leu Ser Asn Tyr Cys
            35                  40                  45

Gly Gly Thr Tyr Glu Gly Ile Thr Lys His Leu Asp Tyr Ile Ser Gly
        50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Gly Val Phe Ala Thr Gly
210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285
```

```
Asp Asn His Asp Asn Pro Arg Phe Leu Asn Ser Gln Ser Asp Lys Ala
        290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                325                 330                 335

Ala Asn Arg Glu Val Leu Trp Thr Thr Asn Tyr Asp Thr Ser Ser Asp
            340                 345                 350

Leu Tyr Gln Phe Ile Lys Thr Val Asn Ser Val Arg Met Lys Ser Asn
        355                 360                 365

Lys Ala Val Tyr Met Asp Ile Tyr Val Gly Asp Asn Ala Tyr Ala Phe
370                 375                 380

Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
                405                 410                 415

Ser Leu Met Asp Ile Val Ser Asn Ile Thr Thr Val Ser Ser Asp
            420                 425                 430

Gly Thr Val Thr Phe Asn Leu Lys Asp Gly Leu Pro Ala Ile Phe Thr
                435                 440                 445

Ser Ala
    450

<210> SEQ ID NO 10
<211> LENGTH: 37
<212> TYPE: PRT
<213> ORGANISM: Aspergillus niger

<400> SEQUENCE: 10

Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
                20                  25                  30

Thr Ser Ser Thr Ser
        35

<210> SEQ ID NO 11
<211> LENGTH: 108
<212> TYPE: PRT
<213> ORGANISM: Aspergillus niger

<400> SEQUENCE: 11

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
                20                  25                  30

Gly Asp Trp Glu Thr Ser Asp Gly Ile Ala Leu Ser Ala Asp Lys Tyr
            35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
                100                 105
```

<210> SEQ ID NO 12
<211> LENGTH: 574
<212> TYPE: PRT
<213> ORGANISM: Artificial Sequence
<220> FEATURE:
<223> OTHER INFORMATION: Hybrid of Meripilus giganteus amylase with A. rolfsii SBD

<400> SEQUENCE: 12

```
Arg Pro Thr Val Phe Asp Ala Gly Ala Asp Ala His Ser Leu His Ala
1               5                   10                  15

Arg Ala Pro Ser Gly Ser Lys Asp Val Ile Ile Gln Met Phe Glu Trp
            20                  25                  30

Asn Trp Asp Ser Val Ala Ala Glu Cys Thr Asn Phe Ile Gly Pro Ala
        35                  40                  45

Gly Tyr Gly Phe Val Gln Val Ser Pro Pro Gln Glu Thr Ile Gln Gly
    50                  55                  60

Ala Gln Trp Trp Thr Asp Tyr Gln Pro Val Ser Tyr Thr Leu Thr Gly
65                  70                  75                  80

Lys Arg Gly Asp Arg Ser Gln Phe Ala Asn Met Ile Thr Thr Cys His
                85                  90                  95

Ala Ala Gly Val Gly Val Ile Val Asp Thr Ile Trp Asn His Met Ala
            100                 105                 110

Gly Val Asp Ser Gly Thr Gly Thr Ala Gly Ser Ser Phe Thr His Tyr
        115                 120                 125

Asn Tyr Pro Gly Ile Tyr Gln Asn Gln Asp Phe His His Cys Gly Leu
    130                 135                 140

Glu Pro Gly Asp Asp Ile Val Asn Tyr Asp Asn Ala Val Glu Val Gln
145                 150                 155                 160

Thr Cys Glu Leu Val Asn Leu Ala Asp Leu Ala Thr Asp Thr Glu Tyr
                165                 170                 175

Val Arg Gly Arg Leu Ala Gln Tyr Gly Asn Asp Leu Leu Ser Leu Gly
            180                 185                 190

Ala Asp Gly Leu Arg Leu Asp Ala Ser Lys His Ile Pro Val Gly Asp
        195                 200                 205

Ile Ala Asn Ile Leu Ser Arg Leu Ser Arg Ser Val Tyr Ile Thr Gln
    210                 215                 220

Glu Val Ile Phe Gly Ala Gly Glu Pro Ile Thr Pro Asn Gln Tyr Thr
225                 230                 235                 240

Gly Asn Gly Asp Val Gln Glu Phe Arg Tyr Thr Ser Ala Leu Lys Asp
                245                 250                 255

Ala Phe Leu Ser Ser Gly Ile Ser Asn Leu Gln Asp Phe Glu Asn Arg
            260                 265                 270

Gly Trp Val Pro Gly Ser Gly Ala Asn Val Phe Val Val Asn His Asp
        275                 280                 285

Thr Glu Arg Asn Gly Ala Ser Leu Asn Asn Ser Pro Ser Asn Thr
    290                 295                 300

Tyr Val Thr Ala Thr Ile Phe Ser Leu Ala His Pro Tyr Gly Thr Pro
305                 310                 315                 320

Thr Ile Leu Ser Ser Tyr Asp Gly Phe Thr Asn Thr Asp Ala Gly Ala
                325                 330                 335

Pro Asn Asn Asn Val Gly Thr Cys Ser Thr Ser Gly Gly Ala Asn Gly
            340                 345                 350

Trp Leu Cys Gln His Arg Trp Thr Ala Ile Ala Gly Met Val Gly Phe
```

```
                355                 360                 365
Arg Asn Asn Val Gly Ser Ala Ala Leu Asn Asn Trp Gln Ala Pro Gln
370                 375                 380

Ser Gln Gln Ile Ala Phe Gly Arg Gly Ala Leu Gly Phe Val Ala Ile
385                 390                 395                 400

Asn Asn Ala Asp Ser Ala Trp Ser Thr Thr Phe Thr Thr Ser Leu Pro
                405                 410                 415

Asp Gly Ser Tyr Cys Asp Val Ile Ser Gly Lys Ala Ser Gly Ser Ser
            420                 425                 430

Cys Thr Gly Ser Ser Phe Thr Val Ser Gly Gly Lys Leu Thr Ala Thr
        435                 440                 445

Val Pro Ala Arg Ser Ala Ile Ala Val His Thr Gly Gln Lys Gly Ser
    450                 455                 460

Gly Gly Gly Ala Thr Ser Pro Gly Gly Ser Gly Ser Val Glu Val
465                 470                 475                 480

Thr Phe Asp Val Tyr Ala Thr Thr Val Tyr Gly Gln Asn Ile Tyr Ile
                485                 490                 495

Thr Gly Asp Val Ser Glu Leu Gly Asn Trp Thr Pro Ala Asn Gly Val
            500                 505                 510

Ala Leu Ser Ser Ala Asn Tyr Pro Thr Trp Ser Ala Thr Ile Ala Leu
        515                 520                 525

Pro Ala Asp Thr Thr Ile Gln Tyr Lys Tyr Val Asn Ile Asp Gly Ser
    530                 535                 540

Thr Val Ile Trp Glu Asp Ala Ile Ser Asn Arg Glu Ile Thr Thr Pro
545                 550                 555                 560

Ala Ser Gly Thr Tyr Thr Glu Lys Asp Thr Trp Asp Glu Ser
                565                 570

<210> SEQ ID NO 13
<211> LENGTH: 1344
<212> TYPE: DNA
<213> ORGANISM: Thermoascus aurantiacus

<400> SEQUENCE: 13
aagtctaccc agtatcctgt caacatgcgg ctcgttgctt ccctaacggc cttggtggcc    60
ttgtccgtac ctgtctttcc cgctgctgtc aacgtgaagc gtgcttcgtc ctacctggag   120
atcactctga gccaggtcag caacactctg atcaaggccg tggtccagaa cactggtagc   180
gacgagttgt ccttcgttca cctgaacttc ttcaaggacc ccgctcctgt caaaaaggta   240
tcggtctatc gcgatgggtc tgaagtgcag ttcgaggca ttttgagccg ctacaaatcg   300
actggcctct tcgtgacgc ctttacttat ctggctcccg agagtccgt cgaggacgtt   360 tttgatattg cttcgactta cgatctgacc agcggcggcc ctgtaactat ccgtactgag   420
ggagttgttc cctacgccac ggctaacagc actgatattg ccggctacat ctcatactcg   480
tctaatgtgt tgaccattga tgtcgatggc gccgctgctg ccactgtctc caaggcaatc   540
actcctttgg accgccgcac taggatcagt tcctgctccg gcagcagaca gagcgctctt   600
actacggctc tcagaaacgc tgcttctctt gccaacgcag ctgccgacgc ggctcagtct   660
ggatcagctt caaagttcag cgagtacttc aagactactt ctagctctac ccgccagacc   720
gtggctgcgc gtcttcgggc tgttgcgcgg aggcatcttc gtcttcttc gggagccacc   780 acgtactact gcgacgatcc ctacggctac tgttcctcca acgtcctggc ttacaccctg   840
ccttcataca acataatcgc caactgtgac attttctata cttacctgcc ggctctgacc   900
```

```
agtacctgtc acgctcagga tcaagcgacc actgcccttc acgagttcac ccatgcgcct    960
ggcgtctaca gccctggcac ggacgacctg gcgtatggct accaggctgc gatgggtctc   1020
agcagcagcc aggctgtcat gaacgctgac acctacgctc tctatgcgaa tgccatatac   1080
cttggttgct aagcgcagag cggtccattg gcgagttggt cgcggtccag ctctagctgg   1140
gatcggccat ggatggtttg agctctgtaa atgacggtcc cgatcttgca gctttgattc   1200
catctaaacg cgcaggaagg aatattagga tgaggatgtt tctatgagac ggctgtgcgc   1260
agagttccga cgagtgacgg taactatttt tgccatagct acataatgca tctacaagtt   1320
atctaaaaaa aaaaaaaaaa aaaa                                          1344
```

DETOXIFYING PRE-TREATED LIGNOCELLULOSE-CONTAINING MATERIALS

CROSS-REFERENCE TO RELATED APPLICATIONS

This application is a 35 U.S.C. 371 national application of PCT/US08/60766 filed Apr. 18, 2008, which claims priority or the benefit under 35 U.S.C. 119 of U.S. provisional application Nos. 60/913,581 filed on Apr. 24, 2007, 60/946,272 filed on Jun. 26, 2007, and 60/988,949 filed Nov. 19, 2007, the contents of which are fully incorporated herein by reference.

TECHNICAL FIELD

The present invention relates to processes of detoxifying pre-treated lignocellulose-containing material. The invention also relates to processes of producing a fermentation product from lignocellulose-containing material using a fermenting organism including a detoxification process of the invention.

BACKGROUND OF THE INVENTION

Due to the limited reserves of fossil fuels and worries about emission of greenhouse gases there is an increasing focus on using renewable energy sources. Production of fermentation products from lignocellulose-containing material is known in the art and conventionally includes pretreatment, hydrolysis, and fermentation of the lignocellulose-containing material. Pre-treatment results in the release of, e.g., phenolics and furans, from the lignocellulose-containing material that may irreversibly bind enzymes added during hydrolysis and fermentation. These compounds may also be toxic to the fermenting organism's metabolism and inhibit the performance of the fermenting organism.

Detoxification by steam stripping has been suggested but it is a cumbersome and a costly additional process step. It has also been suggested to wash the pre-treated lignocellulose-containing material before hydrolysis. This requires huge amounts of water, that needs to be removed again, and is therefore also costly.

Consequently, there is a need for providing processes for detoxifying pre-treated lignocellulose-containing material suitable for fermentation product production processes.

SUMMARY OF THE INVENTION

The present invention relates to processes of detoxifying pre-treated lignocellulose-containing material. The invention also relates to processes of producing a fermentation product from lignocellulose-containing material using a fermenting organism including a detoxification process of the invention.

In the first aspect the invention relates to processes for detoxifying pre-treated lignocellulose-containing material comprising subjecting the pre-treated lignocellulose-containing material to one or more phenolic compound oxidizing enzymes and/or one or more enzymes exhibiting peroxidase activity.

In the second aspect the invention relates to processes for producing a fermentation product from lignocellulose-containing material comprising the steps of:
(a) pre-treating lignocellulose-containing material;
(b) hydrolyzing;
(c) detoxifying in accordance with a detoxification process of the invention; and
(d) fermenting using a fermenting organism.

The invention also relates to processes for producing a fermentation product from lignocellulose-containing material comprising the steps of:
(i) pre-treating lignocellulose-containing material;
(ii) detoxifying in accordance with the fermentation process of the invention;
(iii) hydrolyzing; and
(iv) fermenting using a fermenting organism.

BRIEF DESCRIPTION OF THE FIGURES

The figure shows the effect of laccase treatment on cellulose conversion.

DETAILED DESCRIPTION OF THE INVENTION

In the first aspect the invention relates to processes of detoxifying pre-treated lignocellulose-containing material suitable for producing a fermentation product.

Lignocellulose-Containing Material

The term "lignocellulose-containing materials" used herein refers to material that primarily consists of cellulose, hemicellulose, and lignin. Such material is often referred to as "biomass".

The structure of lignocellulose is not directly accessible to enzymatic hydrolysis. Therefore, the lignocellulose has to be pre-treated, e.g., by acid hydrolysis under adequate conditions of pressure and temperature, in order to break the lignin seal and disrupt the crystalline structure of cellulose. This causes solubilization and saccharification of the hemicellulose fraction. The cellulose fraction can then be hydrolyzed enzymatically, e.g., by cellulase enzymes or cellulolytic enzymes), to convert the carbohydrate polymers into fermentable sugars which may be fermented into a desired fermentation product, such as ethanol. Optionally the fermentation product is recovered after fermentation, e.g., by distillation.

Any lignocellulose-containing material is contemplated according to the present invention. The lignocellulose-containing material may be any material containing lignocellulose. In a preferred embodiment the lignocellulose-containing material contains at least 30 wt, %, preferably at least 50 wt, %, more preferably at least 70 wt. %, even more preferably at least 90 wt. % lignocellulose. It is to be understood that the lignocellulose-containing material may also comprise other constituents such as cellulosic material, including cellulose and hemicellulose, and may also comprise other constituents such as proteinaceous material, starch, sugars, such as fermentable sugars and/or un-fermentable sugars.

Lignocellulose-containing material is generally found, for example, in the stems, leaves, hulls, husks, and cobs of plants or leaves, branches, and wood of trees. Lignocellulose-containing material can also be, but is not limited to, herbaceous material, agricultural residues, forestry residues, municipal solid wastes, waste paper, and pulp and paper mill residues. It is understood herein that lignocellulose-containing material may be in the form of plant cell wall material containing lignin, cellulose, and hemi-cellulose in a mixed matrix.

In a preferred embodiment the lignocellulose-containing material is corn fiber, rice straw, pine wood, wood chips, poplar, bagasse, paper and pulp processing waste.

Other examples include corn stover, hardwood, such as poplar and birch, softwood, cereal straw, such as wheat straw, switchgrass, municipal solid waste (MSW), industrial organic waste, office paper, or mixtures thereof.

In a preferred embodiment the lignocellulose-containing material is corn stover. In another preferred embodiment the material is corn fiber.

Process of Detoxifying Pre-treated Lignocellulose-Containing Material

When lignocellulose-containing material is pre-treated, degradation products that may inhibit enzymes and/or may be toxic to fermenting organisms are produced. These degradation products severely decrease both the hydrolysis and fermentation rate.

Methods for pre-treating lignocellulose-containing material are well known in the art. Examples of contemplated methods are described below in the section "Pre-treatment".

The present inventors have found that phenolic compound oxidizing enzymes can be used to detoxify pre-treated lignocellulose-containing material. The fermentation time can be reduced as a result of improved performance of the fermenting organism during fermentation. In other words, detoxification in accordance with the invention may result in a shorter "lignocellulose-containing material-to-fermentation product" process time. Furthermore, the need for a washing step after pre-treatment of the lignocellulose-containing material, to remove toxic compounds, and/or adaption of the fermentation organism to the medium/broth can be eliminated. Also, the dosing of the fermentation organism may be reduced.

In a preferred embodiment the pre-treated lignocellulose-containing material may be treated with cellulase (cellulolytic enzymes) and/or hemicellulase (hemicellulolytic enzymes).

Specific examples of detoxifying compounds can be found in the "Detoxifying Compounds"-section below.

In the first aspect the invention relates to processes for detoxifying pre-treated lignocellulose-containing material comprising subjecting the pre-treated lignocellulose-containing material to one or more phenolic compound oxidizing enzymes and/or one or more enzymes exhibiting peroxidase activity.

The pre-treated lignocellulose degradation products include lignin degradation products, cellulose degradation products and hemicellulose degradation products. The pre-treated lignin degradation products may be phenolics in nature.

The hemicellulose degradation products include furans from sugars (such as hexoses and/or pentoses), including xylose, mannose, galactose, rhamanose, and arabinose. Examples of hemicelluloses include xylan, galactoglucomannan, arabinogalactan, arabinoglucuronoxylan, glucuronoxylan, and derivatives and combinations thereof.

Examples of inhibitory compounds, i.e., pre-treated lignocellulose degradation products, include 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallollol, pyrogallol mono methyl ether, vanillyi alcohol, vanillin, isovanillin, vanillic acid, isovanillic acid, homovanillic acid, veratryl alcohol, veratraldehyde, veratric acid, 2-O-methyl gailic acid, syringyl alcohol, syringaldehyde, syringic acid, trimethyl gailic acid, homocatechol, ethyl vanillin, creosol, p-methyl anisol, anisaldehyde, anisic acid, furfural, hydroxymethyl-furfural, 5-hydroxymethylfurfural, formic acid, acetic acid, levulinic acid, cinnamic acid, coniferyl aldehyde, isoeugenol, hydroquinone, eugenol or combinations thereof. Other inhibitory compounds can be found in, e.g., Luo at al., 2002, *Biomass and Bioenergy* 125-138

The detoxification process of the invention may preferably be carried out at a pH that is suitable of the phenolic compound oxidizing enzymes and hydrolyzing enzyme(s) and/or fermenting organism if detoxification is carried out simultaneously with hydrolysis or simultaneously with hydrolysis and fermentation. In one embodiment the pH is between 2 and 7, preferably between 3 and 6, especially between 4 and 5. In a preferred embodiment the temperature during detoxification is a temperature suitable for the phenolic compound oxidizing enzyme(s) and/or enzyme exhibiting peroxidase activity and hydrolyzing enzyme(s) and/or fermenting organism if detoxification is carried out a simultaneous with hydrolysis or simultaneously with hydrolysis and fermentation. In one embodiment the temperature during detoxification is between 25° C. and 70° C., preferably between 30° C. and 60° C. In cases where detoxification is carried out simultaneously with fermentation the temperature will depend on the fermenting organism. For ethanol fermentations with yeast the temperature would be between 26-38° C., such as between 26-34° C. or between 30-36° C., such as around 32° C.

Suitable pHs, temperatures and other process conditions can easily be determined by one skilled in the art.

Detoxifying Enzymes

The detoxifying enzyme(s) may be of any origin including of mammal, plant and microbial origin, such as of bacteria and fungal origin.

Phenolic compound oxidizing enzymes may in preferred embodiments belong to any of the following EC classes including: Catechol oxidase (EC 1.10.3.1), Laccase (EC 1.10.3.2), o-Aminophenol oxidase (1.10.3.4); and Monophenol monooxygenase (1.14.18.1).

The enzyme exhibiting peroxidase activity may in a preferred embodiment belong to any of the following EC classes including those selected from the group consisting of a peroxidase (EC 1.11.1.7), Haloperoxidase (EC1.11.1.8 and EC 1.11.1.10); Lignin peroxidase (EC 1.11.1.14); manganese peroxidase (EC 1.11.1.13); and Lipoxygenase (EC. 1.13.11.12).

Examples of detoxifying enzymes contemplated according to the invention can be found in the "Enzymes"-section below.

Production of Fermentation Products from Lignocellulose-Containing Material

In the second aspect the invention relates to processes of producing fermentation products from lignocellulose-containing material. Conversion of lignocellulose-containing material into fermentation products, such as ethanol, has the advantages of the ready availability of large amounts of feedstock, including wood, agricultural residues, herbaceous crops, municipal solid wastes, etc.

The structure of lignocellulose is not directly accessible to enzymatic hydrolysis. Therefore, the lignocellulose-containing material has to be pre-treated, e.g., by acid hydrolysis under adequate conditions of pressure and temperature, in order to break the lignin seal and disrupt the crystalline structure of cellulose. This causes solubilization of the hemicellulose and cellulose fractions. The cellulose and hemicellulose can then be hydrolyzed enzymatically, e.g., by cellulase enzymes (cellulolytic enzymes), to convert the carbohydrate polymers into fermentable sugars which may be fermented into a desired fermentation product, such as ethanol. Optionally the fermentation product may be recovered, e.g., by distillation.

More precisely the invention relates in this embodiment to processes for producing a fermentation product from lignocellulose-containing material comprising the steps of:
(a) pre-treating lignocellulose-containing material;
(b) hydrolyzing;
(c) detoxifying; and
(d) fermenting using a fermenting organism;
wherein detoxification is carried out in accordance with a detoxification process of the invention. More details on the steps are described below in the sections "Pre-treatment", "Hydrolysis" and "Fermentation".

In another embodiment the invention relates to processes for producing a fermentation product from lignocellulose-containing material comprising the steps of:
(i) pre-treating lignocellulose-containing material;
(ii) detoxifying;
(iii) hydrolyzing; and
(iv) fermenting using a fermenting organism;
wherein detoxification is carried out in accordance with a detoxification process of the invention.

One or more detoxifying enzymes may be added after pre-treatment step (i), but before hydrolysis step (iii). Detoxifying the pre-treated material in step (ii) may be carried out before hydrolysis, but detoxification and hydrolysis may also be carried out simultaneously. The detoxification step (ii) may be carried out separately from hydrolysis. Further hydrolysis step (iii) and fermentation step (iv) may be carried out simultaneously or sequentially. In one embodiment the solids (comprising mainly lignin and unconverted polysaccharides) may, after pre-treating the lignocellulose-containing material in step (i), be removed/separated from the liquor before detoxification. The removed solids and the detoxified liquor may be combined before hydrolysis in step (iii) or simultaneous hydrolysis and fermentation.

The solids may be removed/separated in any suitable way know in the art. In suitable embodiments the solids are removed by filtration, or by using a filter press and/or centrifuge, or the like. The reduced inhibitory effect of the hydrolyzing enzymes is tested in Example 4

Examples of pre-treatment methods, hydrolysis and fermentation conditions for both of above embodiment is described below.

Pre-treatment

The lignocellulose-containing material may be pre-treated in any suitable way. Pre-treatment may be carried out before and/or during hydrolysis and/or fermentation. In a preferred embodiment the pre-treated material is hydrolyzed, preferably enzymatical, before and/or during fermentation and/or before and/or during detoxification. The goal of pre-treatment is to separate and/or release cellulose; hemicellulose and/or lignin and this way improve the rate of hydrolysis. Pre-treatment methods such as wet-oxidation and alkaline pre-treatment targets lignin, while dilute acid and autohydrolysis targets hemicellulose. Steam explosion is an example of a pre-treatment that targets cellulose.

According to the invention pre-treatment in step (a) or (i) may be a conventional pre-treatment step using techniques well known in the art. Examples of suitable pre-treatments are disclosed below. In a preferred embodiment pre-treatment takes place in aqueous slurry.

The lignocellulose-containing material may during pre-treatment be present in an amount between 10-80 wt. %, preferably between 20-70 wt. %, especially between 30-60 wt. %, such as around 50 wt. %, Chemical, Mechanical and/or Biological Pre-treatment The lignocellulose-containing material may according to the invention be chemically, mechanically and/or biologically pre-treated before hydrolysis and/or fermentation. Mechanical treatment (often referred to as physical treatment) may be used alone or in combination with subsequent or simultaneous hydrolysis, especially enzymatic hydrolysis.

Preferably, chemical, mechanical and/or biological pre-treatment is carried out prior to the hydrolysis and/or fermentation. Alternatively, the chemical, mechanical and/or biological pre-treatment may be carried out simultaneously with hydrolysis, such as simultaneously with addition of one or more cellulase enzymes (cellulolytic enzymes), or other enzyme activities mentioned below, to release, e.g., fermentable sugars, such as glucose and/or maltose.

In an embodiment of the invention the pre-treated lignocellulose-containing material may be washed before and/or after detoxification. However, washing is not mandatory and is in a preferred embodiment eliminated.

According to one embodiment of the invention one or more detoxifying enzymes may be added to the pre-treated lignocellulose-containing material in step (c) or (ii). Detoxification step (c) or (ii) and hydrolysis step (b) or (iii) may be carried out either simultaneously or sequentially. The reduced toxic effect on the fermenting organism is shown in Examples 2 and 3.

The steps may in one embodiment be done in one treating solution (i.e., one bath). In one embodiment the hydrolyzing enzyme(s) and the detoxifying enzyme(s) are added simultaneously to the treating solution. In another embodiment the hydrolyzing enzyme(s) are added before the detoxifying enzyme(s). It may be advantageous to complete above 50% of hydrolysis, preferably above 70% of hydrolysis, especially above 90% of hydrolysis before adding the detoxifying enzyme(s) to the treating solution. If the pre-treated lignocellulose-containing material is hydrolyzed enzymatically, it is advantageous to do detoxification before and/or simultaneous with hydrolysis. However, if hydrolysis is carried out using one or more acids, i.e., acid hydrolysis, detoxification is preferably carried out after and/or simultaneously with acid hydrolysis.

In another embodiment detoxification step (c) or (ii) may be carried out separately from hydrolysis step (b) or (iii) and fermentation step (d) or (iv), respectively, which in one embodiment may be carried out simultaneously. In a further embodiment all of steps (b), (c) and (d) or (i), (ii), (iii) and (iv), respectively, are carried out simultaneously or sequentially. When detoxification is done as a separate step, it typically is carried out for between 1-24 hours.

In a preferred embodiment the pre-treated lignocellulose-containing material is unwashed.

In an embodiment the phenolic compound oxidizing enzyme(s) is(are) dosed in the range from above 0, such as 0.01 to 1 mg/g DS or in the range from above 0 to 100 LACU/g DS. In an embodiment the enzyme(s) exhibiting peroxidase activity is(are) dosed in the range from above 0, such as 0.01 to 10 mg/g DS or above 0, such as 0.01 to 100 PODU/g DS.

Chemical Pre-treatment

The term "chemical treatment" refers to any chemical pre-treatment which promotes the separation and/or release of cellulose, hemicellulose and/or lignin. Examples of suitable chemical pre-treatments include treatment with for example, dilute acid, lime, alkaline, organic solvent, ammonia, sulfur dioxide, carbon dioxide. Further, wet oxidation and pH-controlled hydrothermolysis are also considered chemical pre-treatment.

In a preferred embodiment the chemical pre-treatment is acid treatment, more preferably, a continuous dilute and/or mild acid treatment, such as, treatment with sulfuric acid, or another organic acid, such as acetic acid, citric acid, tartaric acid, succinic acid, hydrogen chloride or mixtures thereof. Other acids may also be used. Mild acid treatment means that the treatment pH lies in the range from 1-5, preferably 1-3. In a specific embodiment the acid concentration is in the range from 0.1 to 2.0 wt. % acid, preferably sulphuric acid. The acid may be contacted with the lignocellulose-containing material and the mixture may be held at a temperature in the range of 160-220° C., such as 165-195° C., for periods ranging from minutes to seconds, e.g., 1-60 minutes, such as 2-30 minutes or 3-12 minutes. Addition of strong acids, such as sulphuric acid, may be applied to remove hemicellulose. This enhances the digestibility of cellulose.

Other techniques are also contemplated. Cellulose solvent treatment has been shown to convert about 90% of cellulose to glucose. It has also been shown that enzymatic hydrolysis could be greatly enhanced when the lignocellulose structure is disrupted. Alkaline $H_2O_2$, ozone, organosolv (uses Lewis acids, $FeCl_3$, $(Al)_2SO_4$ in aqueous alcohols), glycerol, dioxane, phenol, or ethylene glycol are among solvents known to disrupt cellulose structure and promote hydrolysis (Mosier et al., 2005, *Bioresource Technology* 96: 673-686).

Alkaline chemical pre-treatment with base, e.g., NaOH, $Na_2CO_3$ and/or ammonia or the like, is also contemplated according to the invention. Pre-treatment methods using ammonia are described in, e.g., WO 2006/110891, WO 2006/110899, WO 2006/110900, and WO 2006/110901 (which are hereby incorporated by reference).

Wet oxidation techniques involve use of oxidizing agents, such as: sulphite based oxidizing agents or the like, examples of solvent pre-treatments include treatment with DMSO (Dimethyl Sulfoxide) or the like. Chemical pre-treatment is generally carried out for 1 to 60 minutes, such as from 5 to 30 minutes, but may be carried out for shorter or longer periods of time dependent on the material to be pre-treated.

Other examples of suitable pre-treatment methods are described by Schell et al., 2003, *Appl. Biochem and Biotechn.* Vol. 105-108: 69-85, and Mosier et al., 2005, *Bioresource Technology* 96: 673-686, and U.S. Publication No. 2002/0164730, which references are hereby all incorporated by reference.

Mechanical Pre-treatment

The term "mechanical pre-treatment" refers to any mechanical (or physical) treatment which promotes the separation and/or release of cellulose, hemicellulose and/or lignin from lignocellulose-containing material. For example, mechanical pre-treatment includes various types of milling, irradiation, steaming/steam explosion, and hydrothermolysis.

Mechanical pre-treatment includes comminution (mechanical reduction of the size). Comminution includes dry milling, wet milling and vibratory ball milling. Mechanical pre-treatment may involve high pressure and/or high temperature (steam explosion). In an embodiment of the invention high pressure means pressure in the range from 300 to 600 psi, preferably 400 to 500 psi, such as around 450 psi. In an embodiment of the invention high temperature means temperatures in the range from about 100 to 300° C., preferably from about 140 to 235° C. In a preferred embodiment mechanical pre-treatment is a batch-process, steam gun hydrolyzer system which uses high pressure and high temperature as defined above. A Sunds Hydrolyzer (available from Sunds Defibrator AB (Sweden) may be used for this.

Combined Chemical and Mechanical Pre-treatment

In a preferred embodiment both chemical and mechanical pre-treatments are carried out. For instance, the pre-treatment step may involve dilute or mild acid treatment and high temperature and/or pressure treatment. The chemical and mechanical pre-treatment may be carried out sequentially or simultaneously, as desired.

Accordingly, in a preferred embodiment, the lignocellulose-containing material is subjected to both chemical and mechanical pre-treatment to promote the separation and/or release of cellulose, hemicellulose and/or lignin.

In a preferred embodiment the pre-treatment is carried out as a dilute and/or mild acid steam explosion step. In another preferred embodiment pre-treatment is carried out as an ammonia fiber explosion step (or AFEX pre-treatment step).

Biological Pre-treatment

As used in the present invention the term "biological pre-treatment" refers to any biological pre-treatment which promotes the separation and/or release of cellulose, hemicellulose, and/or lignin from the lignocellulose-containing material. Biological pre-treatment techniques can involve applying lignin-solubilizing microorganisms (see, for example, Hsu, 1996, Pretreatment of biomass, in *Handbook on Bioethanol: Production and Utilization*, Wyman, ed., Taylor & Francis, Washington, D.C., 179-212; Ghosh and Singh, 1993, Physicochemical and biological treatments for enzymatic/microbial conversion of lignocellulosic biomass, *Adv. Appl. Microbial* 39: 295-333: McMillan, 1994, Pre-treating lignocellulosic biomass: a review, in *Enzymatic Conversion of Biomass for Fuels Production*, Himmel, Baker, and Overend, eds., ACS Symposium Series 566, American Chemical Society, Washington. D.C., chapter 15; Gong, Cao, Du, and Tsao, 1999, Ethanol production from renewable resources, in *Advances in Biochemical Engineering/Biotechnology*, Scheper, ed., Springer-Verlag Berlin Heidelberg, Germany, 65: 207-241 Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials; State of the art, *Adv. Biochem. Eng./Biotechnol,* 42: 63-95), Hydrolysis Before and/or simultaneously with fermentation the pre-treated lignocellulose-containing material may be hydrolyzed to break down cellulose and hemicellulose.

The dry solids content during hydrolysis may be in the range from 5-50 wt. %, preferably 10-40 wt. %, preferably 20-30 wt. %. Hydrolysis may in a preferred embodiment be carried out as a fed batch process where the pre-treated lignocellulose-containing material (substrate) is fed gradually to an, e.g., enzyme containing hydrolysis solution.

In an embodiment of the invention detoxification takes place before, during and/or after hydrolysis.

In a preferred embodiment hydrolysis is carried out enzymatically. According to the invention the pre-treated lignocellulose-containing material may be hydrolyzed by one or more hydrolases (class EC 3 according to Enzyme Nomenclature), preferably one or more carbohydrases selected from the group consisting of cellulase, hemicellulase, amylase, such as alpha-amylase, protease, carbohydrate-generating enzyme, such as glucoamylase, esterase, such as lipase. Alpha-amylase, glucoamylase and/or the like may be present during hydrolysis and/or fermentation as the lignocellulose-containing material may include some starch.

The enzyme(s) used for hydrolysis is(are) capable of directly or indirectly converting carbohydrate polymers into fermentable sugars which can be fermented into a desired fermentation product, such as ethanol.

In a preferred embodiment the carbohydrase has cellulase enzyme activity. Suitable carbohydrases are described in the "Enzymes"-section below.

Hemicellulose polymers can be broken down by hemicellulases and/or acid hydrolysis to release its five and six carbon sugar components. The six carbon sugars (hexoses), such as glucose, galactose, arabinose, and mannose, can readily be fermented to e.g., ethanol, acetone, butanol, glycerol, citric acid, fumaric acid, etc. by suitable fermenting organisms including yeast. Preferred for ethanol fermentation is yeast of the species *Saccharomyces cerevisiae*, preferably strains which are resistant towards high levels of ethanol, i.e. up to, e.g. about 10, 12 or 15 vol. % ethanol or more, such as 20 vol. % ethanol.

In a preferred embodiment the pre-treated lignocellulose-containing material is hydrolyzed using a hemicellulase, preferably a xylanase, esterase, cellobiase, or combination thereof.

Hydrolysis may also be carried out in the presence of a combination of hemicellulases and/or cellulases, and optionally one or more of the other enzyme activities mentioned in the "Enzyme" section below.

In a preferred embodiment hydrolysis and fermentation is carried out as a simultaneous hydrolysis and fermentation step (SSF). In general this means that combined/simultaneous hydrolysis and fermentation are carried out at conditions (e.g., temperature and/or pH) suitable, preferably optimal, for the fermenting organism(s) in question.

In another preferred embodiment hydrolysis and fermentation are carried out as hybrid hydrolysis and fermentation (HHF). HHF typically begins with a separate partial hydrolysis step and ends with a simultaneous hydrolysis and fermentation step. The separate partial hydrolysis step is an enzymatic cellulose saccharification step typically carried out at conditions (e.g., at higher temperatures) suitable, preferably optimal, for the hydrolyzing enzyme(s) in question. The subsequent simultaneous hydrolysis and fermentation step is typically carried out at conditions suitable for the fermenting organism(s) (often at lower temperatures than the separate hydrolysis step). Finally, hydrolysis and fermentation may also be carried out a separate hydrolysis and fermentation, where the hydrolysis is taken to completion before initiation of fermentation. This often referred to as "SHF".

Enzymatic treatments may be carried out in a suitable aqueous environment under conditions which can readily be determined by one skilled in the art.

In a preferred embodiment hydrolysis is carried out at suitable, preferably optimal conditions for the enzyme(s) in question.

Suitable process time, temperature and pH conditions can readily be determined by one skilled in the art present invention. Preferably, hydrolysis is carried out at a temperature between 25 and 70° C., preferably between 40 and 60° C., especially around 50° C. The process is preferably carried out at a pH in the range from 3-8, preferably pH 4-6, especially around pH 5.

Preferably, hydrolysis is carried out for between 12 and 96 hours, preferable 16 to 72 hours, more preferably between 24 and 48 hours.

According to the invention hydrolysis in step (b) or (iii) and fermentation in step (d) or (iv) may be carried out simultaneously (SSF process) or sequentially (SHF process) or as a hybrid hydrolysis and fermentation (HHF).

Fermentation

According to the invention the pre-treated (and hydrolyzed) lignocellulose-containing material is fermented by at least one fermenting organism capable of fermenting fermentable sugars, such as glucose, xylose, mannose, and galactose directly or indirectly into a desired fermentation product.

The fermentation is preferably ongoing for between 8 to 98 hours, preferably 12 to 72 hours, more preferable from 24 to 48 hours.

In an embodiment the fermentation is carried out at a temperature between 20 to 40° C., preferably 26 to 34° C., in particular around 32° C. In an embodiment the pH is from pH 3 to 6, preferably around pH 4 to 5.

Contemplated according to the invention is simultaneous hydrolysis and fermentation (SSF). In an embodiment there is no separate holding stage for the hydrolysis, meaning that the hydrolyzing enzyme(s) and the fermenting organism are added together. When the fermentation (e.g., ethanol fermentation using *Saccharomyces* yeast) is performed simultaneous with hydrolysis the temperature is preferably between 26° C. and 35° C., more preferably between 30° C. and 34° C., such as around 32° C. A temperature program comprising at least two holding stages at different temperatures may be applied according to the invention.

The process of the invention may be performed as a batch, fed-batch or as a continuous process.

Recovery

Subsequent to fermentation the fermentation product may be separated from the fermentation medium/broth. The medium/broth may be distilled to extract the fermentation product or the fermentation product may be extracted from the fermentation medium/broth by micro or membrane filtration techniques. Alternatively the fermentation product may be recovered by stripping. Recovery methods are well known in the art.

Fermentation Products

Processes of the invention may be used for producing any fermentation product. Especially contemplated fermentation products include alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones.

Also contemplated products include consumable alcohol industry products, e.g., beer and wine; dairy industry products, e.g., fermented dairy products; leather industry products and tobacco industry products. In a preferred embodiment the fermentation product is an alcohol, especially ethanol. The fermentation product, such as ethanol, obtained according to the invention, may preferably be fuel alcohol/ethanol. However, in the case of ethanol it may also be used as potable ethanol.

Fermenting Organism

The term "fermenting organism" refers to any organism, including bacterial and fungal organisms, suitable for producing a desired fermentation product. Especially suitable fermenting organisms according to the invention are able to ferment, i.e., convert, sugars, such as glucose, directly or indirectly into the desired fermentation product. Examples of fermenting organisms include fungal organisms, such as yeast. Preferred yeast includes strains of the genus *Saccharomyces*, in particular a strain of *Saccharomyces cerevisiae* or *Saccharomyces uvarum*; a strain of *Pichia*, in particular

*Pichia stipitis* or *Pichia pastoris*; a strain of the genus *Candida*, in particular a strain of *Candida utilis, Candida arabinofermentans, Candida diddensii*, or *Candida boidinii*. Other contemplated yeast includes strains of *Hansenula*, in particular *Hansenula polymorpha* or *Hansenula anomala*; strains of *Kluyveromyces*, in particular *Kluyveromyces marxianus* or *Kluyveromyces fagilis*, and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter* in particular *Zymobactor palmae*, strains of *Klebsiella*, in particular *Klebsiella oxytoca*, strains of *Leuconostoc*, in particular *Leuconostoc mesenteroides*, strains of *Clostridium*, in particular *Clostridium butyricum*, strains of *Enterobacter* in particular *Enterobacter aerogenes* and strains of *Thermoanaerobacter*, in particular *Thermoanaerobacter* BG1L1 (*Appl. Micrbiol. Biotech.* 77: 61-86) and *Thermoanarobacter ethanolicus*.

Commercially available yeast includes, e.g., RED STAR™ or ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Enzymes

Even though not specifically mentioned in context of processes of the invention, it is to be understood that the enzymes (as well as other compounds) are used in an "effective amount". For instance, "effective amount" means, in context of phenolic compound oxidizing enzyme(s) that it has an improving effect compared to a corresponding process where no phenolic compound oxidizing enzyme(s) was (were) added.

Phenolic Compound Oxidizing Enzymes

Preferred phenolic compound oxidizing enzymes belong to any of the following EC classes: Catechol oxidase (EC 1.10.3.1), Laccase (EC 1.10.3.2), o-Aminophenol oxidase (1.10.3.4); and Monophenol monooxygenase (1.14.18.1).

Laccase

Laccases (EC 1.10.3.2) are multi-copper-containing enzymes that catalyze the oxidation of phenolic compounds. Laccases are produced by plants, bacteria and also a wide variety of fungi, including Ascomycetes such as *Aspergillus, Neurospora*, and *Podospora*; Deuteromycete including *Botrytis*, and Basidiomycetes such as *Collybia, Fomes, Lentinus, Pleuratus, Tremetes*, and perfect forms of *Rhizoctonia*. A number of fungal laccases have been isolated. For example, Choi et al. (*Mol. Plant-Microbe Interactions* 5: 119-128, 1992) describe the molecular characterization and cloning of the gene encoding the laccase of the chestnut blight fungus, *Cryphonectria parasitica*. Kojima et al. (*J. Biol. Chem.* 265: 15224-15230, 1990; JP 2-238885) provide a description of two allelic forms of the laccase of the white-rot basidiomycete *Coriolus hirsutus*. Germann and Lerch (*Experientia* 41: 801, 1985. *PNAS USA* 83: 8854-8858, 1986) have reported the cloning and partial sequencing of the *Neurospora crassa* laccase gene. Saloheimo et al. (*J. Gen. Microbiol.* 137: 1537-1544, 1985; WO 92/01046) have disclosed a structural analysis of the laccase gene from the fungus *Phlebia radiata*.

Especially contemplated laccases include those derived from a strain of *Polyporus*, preferably *Polyporus pinsitus*; *Melanocarpus*, preferably *Melanocarpus albomyces*; *Myceliophtora*, preferably *Myceliophtora thermophila*; *Coprinus*, preferably *Coprinus cinereus*; *Rhizoctonia*, preferably *Rhizoctonia solani* or *Rhizoctonia praticola*; *Scytalidium*, preferably *Scytalidium thermophilum*; *Pyricularia*, preferably *Pyricularia oryzae*.

In an embodiment the laccase is derived from the tree *Rhus vernicifera* (Yoshida, 1983, Chemistry of Lacquer (Urushi) part 1. *J. Chem. Soc.* 43: 472-486).

In another embodiment the laccase is derived from *Myceliopthora thermophila*, e.g., the one described in WO 95/33836 (Novozymes).

In another embodiment the laccase is derived from *Polyporus pinsitus*, e.g., the one described in WO 96/00290 (Novozymes).

Jönsson et al., 1998, *Appl, Microbial. Biotechnol*, 49: 691-697, also discloses a suitable laccase derived from *Polyporus versicolar*.

Other laccases include the one derived from *Pyricularia oryzae* concerned in, e.g., Muralikrishna et al., 1995, *Appl, Environ, Microbial.* 61(12): 4374-4377, or the laccase derived from *Scytalidium thermaphilum*, which is disclosed in Abstract of Papers American Chemical Society vol. 209, no. 1-2, 1995.

The laccase may also be one derived from *Coprinus cinereus*, e.g., the one concerned in Schneider at al., 1999, *Enzyme and Microbial Technology* 25: 502-508.

Other suitable laccases include those derived from *Rhizoctonia solani* concerned in Waleithner et al., *Curr. Genet.*, 1996, 29: 395-403, or derived from *Melanocarpus albomyces* concerned in Kiiskinen et al., 2004, *Microbiology* 150: 3065-3074.

Suitable bacterial laccase include those derived from *Streptomyces coelicolor*, e.g., disclosed by Machczynski et al, in *Protein Science*, 2004, 13: 2388-2397, Enzymes Exhibiting Peroxidase Activity According to the invention any enzyme exhibiting peroxidase activity may be used.

The enzyme exhibiting peroxidase activity may be selected from the group consisting of a peroxidase (EC 1.11.1.7), haloperoxidase (EC1.11.1.8 and EC 1.11.1.10), lignin perocidase (EC 1.11.1.14), manganese peroxidase (EC 1.11.1.13); and lipoxygenase (EC.1.13.11.12), Peroxidase The enzyme exhibiting peroxidase activity may be any peroxidase classified as EC 1.11.1.7.

Peroxidases suitable in processes of the invention may be of plant (e.g., horseradish or soybean peroxidase), or microbial origin, such as of fungal or bacteria origin. Examples include peroxidases derived from fungi of the subdivision Deuteromycotina, class Hyphomycetes. e.g. *Fusarium, Humicola, Tricoderma, Myrothecium, Verticillum, Arthromyces, Caldariomyces, Ulocladium, Embellisia, Cladosporium* or *Dreschlera*, in particular *Fusarium oxysporum* (DSM 2672), *Humicola insolens, Trichoderma reesii, Myrothecium verrucana* (IFO 6113), *Verticillum alboatrum, Verticillum dahlia, Arthromyces ramosus* (FERM P-7754), *Caldariomyces fumago, Ulociadium chartarum, Embellisia alli* or *Dreschlera halodes*.

Other suitable peroxidases are derived from fungi including strains of the subdivision Basidiomycotina, class Basidiomycetes, e.g., *Coprinus, Phanerochaete, Coriolus* or *Trametes*, in particular *Coprinus cinereus* f. *microsporus* (IFO 8371), *Coprinus macrorhizus, Phanerochaete chrysosporium* (e.g. NA-12) or *Trametes* (previously called *Polyporus*), e.g., *T. versicolor* (e.g., PR428-A).

Other peroxidases may be derived from fungi including strains belonging to the subdivision Zygomycotina, class Mycoraceae, e.g., *Rhizopus* or *Mucor*, in particular *Mucor hiemalis*.

Bacterial peroxidases may be derived from strains of the order Actinomycetales, e.g., *Streptomyces spheroides* (ATTC 23965), *Streptomyces thermoviolaceus* (IFO 12382) or *Streptoverticillum verticillum* ssp. *Verticillium, Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11): *Myxococcus*, e.g., *M. virescens*.

Recombinantly produced peroxidases derived from *Coprinus* sp., in particular *C. macrorhizus* or *C. cinereus* are described in WO 92/16634. Variants thereof are described in WO 94/12621.

Haloperoxidase

The enzyme exhibiting peroxidase activity may be any haloperoxidase. Haloperoxidases are widespread in nature and are known to be produced by mammals, plants, algae, lichen, bacteria, and fungi. There are three types of haloperoxidases, classified according to their specificity for halide ions; Chloroperoxidases (E.C. 0.11.1.10) which catalyze the chlorination, bromination and iodination of compounds; bromoperoxidases which show specificity for bromide and iodide ions; and iodoperoxidases (E.C. 1.11.1.8) which solely catalyze the oxidation of iodide ions.

Haloperoxidases include the haloperoxidase from *Curvularia*, in particular, *C. verruculosa*, such as, *C. verruculosa* CBS 147.63 or *C. verruculosa* CBS 444.70. *Curvularia* haloperoxidase and recombinant production hereof is described in WO97/04102. Bromide peroxidase has been isolated from algae (see U.S. Pat. No. 4,937,192). Haloperoxidases are also described in U.S. Pat. No. 6,372,465 (Novozymes A/S).

In a preferred embodiment, the haloperoxidase is a chloroperoxidase (E.C. 1.11.1.10). Chloroperoxidases are known in the art and may be obtained from *Streptomyces aureofaciens, Streptomyces lividans, Pseudomonas fluorescens, Caldariomyces fumago, Curvularia inaequalis*, and *Corallina officinalis*, A preferred chloroperoxidase is the chloroperoxidase from *Caldariomyces fumago* (available from SIGMA, C-0278).

Haloperoxidases containing a vanadium prosthetic group are known to include at least two types of fungal chloroperoxidases from *Curvularia inaequalis* (van Schijndel et al., 1993, *Biochimica Biophysica Acta* 1161:249-256; Simons et al., 1995, *European Journal of Biochemistry* 229: 566-574; WO 95/27046) and *Curvularia verruculosa* (WO 97/04102) or *Phaeotrichoconis crotalariae* haloperoxidase (WO 2001/079461)

Lipoxygenase (LOX)

The enzyme exhibiting peroxidase activity may be any lipoxygenase (LOX). Lipoxygenases are classified as EC 1.13.11.12, which is an enzyme that catalyzes the oxygenation of polyunsaturated fatty acids, especially cis,cis-1,4-dienes, e.g., linoleic acid and produces a hydroperoxide. But also other substrates may be oxidized, e.g., monounsaturated fatty acids. Microbial lipoxygenases may be derived from, e.g. *Saccharomyces cerevisiae, Thermoactinomyces vulgaris, Fusarium oxysporum, Fusarium proliferatum, Thermomyces lanuginosus, Pyricularia oryzae*, and strains of *Geotrichum*. The preparation of a lipoxygenase derived from *Gaeumannomyces graminis* is described in Examples 3-4 of WO 02/20730. The expression in *Aspergillus oryzae* of a lipoxygenase derived from *Magnaporthe salvinii* is described in Example 2 of WO 02/086114, and this enzyme can be purified using standard methods, e.g., as described in Example 4 of WO 02/20730.

Lipoxygenase (LOX) may also be extracted from plant seeds, such as soybean, pea, chickpea, and kidney bean. Alternatively, lipoxygenase may be obtained from mammalian cells, e.g., rabbit reticulacytes.

Cellulases or Cellulolytic Enzymes

The term "cellulases" or "cellulolytic enzymes" as used herein are understood as comprising the cellobiohydrolases (EC 3.2.1.91), e.g., cellobiohydrolase I and cellobiohydrolase II, as well as the endo-glucanases (EC 3.2, 1.4), and beta-glucosidases (EC 3.2.1.21).

In order to be efficient, the digestion of cellulose and hemicellulose requires several types of enzymes acting cooperatively. At least three categories of enzymes are important to convert cellulose into fermentable sugars: endo-glucanases (EC 3.2.1.4) cut cellulose chains at random; cellobiohydrolases (EC 3.2.1.91) cleave cellobiosyl units from the cellulose chain ends and beta-glucosidases (EC 3.2.1.21) convert cellobiose and soluble cellodextrins into glucose. Among these three categories of enzymes involved in the biodegradation of cellulose, cellobiohydrolases are the key enzymes for the degradation of native crystalline cellulose. The term "cellobiohydrolase I" is defined herein as a cellulose 1,4-beta-cellobiosidase (also referred to as exo-glucanase, exo-cellobiohydrolase or 1,4-beta-cellobiohydrolase) activity, as defined in the enzyme class EC 3.2.1.91, which catalyzes the hydrolysis of 1,4-beta-D-glucosidic linkages in cellulose and cellotetraose, by the release of cellobiose from the non-reducing ends of the chains. The definition of the term "cellobiohydrolase II activity" is identical, except that cellobiohydrolase II attacks from the reducing ends of the chains.

Endoglucanases (EC No. 3.21.4) catalyze endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucano hydrolase, but the abbreviated term endoglucanase is used in the present specification.

The cellulases or cellulolytic enzymes may comprise a carbohydrate-binding module (CBM) which enhances the binding of the enzyme to a cellulose-containing fiber and increases the efficacy of the catalytic active part of the enzyme. A CBM is defined as contiguous amino acid sequence within a carbohydrate-active enzyme with a discreet fold having carbohydrate-binding activity. For further information on CBMs see, e.g., the CAZy internet server (Supra) or Tomme et al., 1995, in Enzymatic Degradation of Insoluble Polysaccharides (Saddler & Penner, eds.), Cellulose-binding domains: classification and properties. pp. 142-163, American Chemical Society, Washington.

The cellulase activity may, in a preferred embodiment, be derived from a fungal source, such as a strain of the genus *Trichoderma*, preferably a strain of *Trichoderma reesei*, a strain of the genus *Humicola*, such as a strain of *Humicola insofens*; or a strain of *Chrysosporium*, preferably a strain of *Chrysosporium lucknowense*.

In a preferred embodiment cellulase or cellulolytic enzyme preparation is a composition concerned in co-pending application U.S. provisional application No. 60/941,251, which is hereby incorporated by reference. In a preferred embodiment the cellulase or cellulolytic enzyme preparation comprising a polypeptide having cellulolytic enhancing activity, preferably a family GH61A polypeptide, preferably one disclosed in WO 2005/074656 (Novozymes). The cellulolytic enzyme preparation may further comprise a beta-glucosidase, such as a beta-glucosidase derived from a strain of the genus *Trichoderma, Aspergillus*, or *Penicillium*, including the fusion protein having beta-glucosidase activity disclosed in U.S. provisional application No. 60/832,511 (PCT/US2007/074038) (Novozymes). In a preferred embodiment the cellulolytic enzyme preparation may also comprises a CBH II enzyme, preferably *Thielavia terrestris* cellobiohydrolase II (CEL6A). In another preferred embodiment the cellulolytic enzyme preparation may also comprise cellulolytic enzymes, preferably one derived from *Trichoderma reesei* or *Humicola insolens*.

In a specific embodiment the cellulolytic enzyme preparation may also comprise a polypeptide having cellulolytic enhancing activity (GH61A) disclosed in WO 2005/074656; a CBH II from *Thielavia terrestris* cellobiohydrolase II (CEL6A); and a beta-glucosidase (fusion protein disclosed in U.S. provisional application No. 60/832,511 (or PCT/US2007/074038)), and cellulolytic enzymes derived from *Trichoderma reesei*.

In another specific embodiment the cellulolytic enzyme preparation may also comprise a polypeptide having cellulolytic enhancing activity (GH61A) disclosed in WO 2005/074656; a beta-glucosidase (fusion protein disclosed in U.S. provisional application no. 60/832,511 (or PCT/US2007/074038)), and cellulolytic enzymes derived from *Trichoderma reesei*.

In preferred embodiments the cellulase or cellulolytic preparations are Cellulolytic preparations A and B used in Examples 1 and 4, respectively, disclosed in U.S. provisional application No. 60/941,251.

In an embodiment the cellulase is the commercially available product CELLUCLAST® 1.5L or CEL-LUZYME™ (Novozymes A/S, Denmark) or ACCEL-ERASE™ 1000 (from Genencor Inc., USA).

A cellulase or cellulolytic enzyme may be added for hydrolyzing the pre-treated lignocellulose-containing material. The cellulase may be dosed in the range from 0.1-100 FPU per gram total solids (TS), preferably 0.5-50 FPU per gram TS, especially 1-20 FPU per gram TS.

Hemicellulases

Hemicellulose can be broken down by hemicellulases and/or acid hydrolysis to release its five and six carbon sugar components. In an embodiment of the invention the lignocellulose derived material may be treated with one or more hemicellulase.

Any hemicellulase suitable for use in hydrolyzing hemicellulose may be used. Preferred hemicellulases include xylanases, arabinofuranosidases, acetyl xylan esterase, feruloyl esterase, glucuronidases, endo-galactanase, mannases, endo or exo arabinases, exo-galactanases, and mixtures of two or more thereof. Preferably, the hemicellulase for use in the present invention is an exo-acting hemicellulase, and more preferably, the hemicellulase is an exo-acting hemicellulase which has the ability to hydrolyze hemicellulose under acidic conditions of below pH 7, preferably pH 3-7. An example of hemicellulase suitable for use in the present invention includes VISCOZYME™ (available from Novozymes A/S, Denmark).

Arabinofuranosidase (EC 321.55) catalyzes the hydrolysis of terminal non-reducing alpha-L-arabinofuranoside residues in alpha-L-arabinosides.

Galactanase (EC 3.2.1.89), arabinogalactan endo-1,4-beta-galactosidase, catalyzes the endohydrolysis of 1,4-D-galactosidic linkages in arabinogalactans.

Pectinase (EC 3.2.1.15) catalyzes the hydrolysis of 1,4-alpha-D-galactosiduronic linkages in pectate and other galacturonans.

Xyloglucanase catalyzes the hydrolysis of xyloglucan.

The hemicellulase may be added in an amount effective to hydrolyze hemicellulose, such as, in amounts from about 0.001 to 0.5 wt. % of total solids ES), more preferably from about 0.05 to 0.5 wt. % of TS.

Alpha-Amylase

According to the invention an alpha-amylase may be used. In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylase

According to the invention the bacterial alpha-amylase is preferably derived from the genus *Bacillus*.

In a preferred embodiment the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase shown in SEQ ID NO: 1, the *Bacillus amyloliquefaciens* alpha-amylase SEQ ID NO: 2 and the *Bacillus stearothermophilus* alpha-amylase shown in SEQ ID NO: 3 (all sequences hereby incorporated by reference). In an embodiment of the invention the alpha-amylase may be an enzyme having a degree of identity of at least 60%, preferably at least 70%, more preferred at least 80%, even more preferred at least 90%, such as at least 95%, at least 96%, at least 97%, at least 98% or at least 99% to any of the sequences shown in SEQ ID NOS: 4, 5 or 3, respectively.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873- see e.g., page 20, lines 1-10 (hereby incorporated by reference), preferably corresponding to delta(181-182) compared to the wild-type BSG alpha-amylase amino acid sequence set forth in SEQ ID NO:3 or deletion of amino acids R179 and G180 using SEQ ID NO:3 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181* +G182* +N193F) compared to the wild-type BSG alpha-amylase amino acid sequence set forth in SEQ ID NO:3.

Bacterial Hybrid Alpha-Amylase

A hybrid alpha-amylase specifically contemplated comprises 445 C-terminal amino acid residues of the *Bacillus licheniformis* alpha-amylase (shown in SEQ ID NO: 1) and the 37 N-terminal amino acid residues of the alpha-amylase derived from *Bacillus amyloliquefaciens*(shown in SEQ ID NO: 2), with one or more, especially all, of the following substitution:

G48A+T49I+G107A+H156Y+A181T+N190F+I201F+ A209V+Q264S (using the *Bacillus licheniformis* numbering in SEQ ID NO: 1). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 2 numbering).

Fungal Alpha-Amylase

Fungal alpha-amylases include alpha-amylases derived from a strain of the genus *Aspergillus*, such as, *Aspergillus oryzae, Aspergillus niger* and *Aspergillis kawachii* alpha-amylases.

A preferred acidic fungal alpha-amylase is a Fungamyl-like alpha-amylase which is derived from a strain of *Aspergillus oryzae*. According to the present invention, the term "Fungamyl-like alpha-amylase" indicates an alpha-amylase which exhibits a high identity, i.e., more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 6.

Another preferred acidic alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no, P56271 and described in WO 89/01969 (Example 3). A commercially available acid fungal alpha-amylase derived from *Aspergillus niger* is SP288 (available from Novozymes A/S, Denmark).

Other contemplated wild-type alpha-amylases include those derived from a strain of the genera *Rhizomucor* and *Meripilus*, preferably a strain of *Rhizemucor pusillus* (WO 2004/055178 incorporated by reference) or *Meripilus giganteus*.

In a preferred embodiment the alpha-amylase is derived from *Aspergillus kawachii* and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL:#AB008370.

The fungal alpha-amylase may also be a wild-type enzyme comprising a starch-binding domain (SBD) and an alpha-amylase catalytic domain (i.e., non-hybrid), or a variant thereof. In an embodiment the wild-type alpha-amylase is derived from a strain of *Aspergillus kawachii*.

Fungal Hybrid Alpha-Amylase

In a preferred embodiment the fungal acid alpha-amylase is a hybrid alpha-amylase. Preferred examples of fungal hybrid alpha-amylases include the ones disclosed in WO 2005/003311 or U.S. Publication No. 2005/0054071 (Novozymes) or U.S. provisional application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. provisional application no. 60/638,614, including Fungamyl variant with catalytic domain JA118 and *Athelia rolfsii* SBD (SEQ ID NO: 7), *Rhizomucor pusiflus* alpha-amylase with *Athelia rolfsII* AMG linker and SBD (SEQ ID NO: 8), *Rhizomucor pusillus* alpha-amylase with *Aspergillus niger* glucoamylase linker and SBD (which is disclosed in Table 5 as a combination of amino acid sequences SEQ ID NO: 9, SEQ ID NO: 10 and SEQ ID NO: 11) or as V039 in Table 5 in WO 2006/069290, and *Meripilus giganteus* alpha-amylase with *Athelia rolfsii* glucoamylase linker and SBD (SEQ ID NO: 12). Other specifically contemplated hybrid alpha-amylases are any of the ones listed in Tables 3, 4, 5, and 6 in Example 4 in U.S. application Ser. No. 11/316,535 and WO 2006/069290 (hereby incorporated by reference).

Other specific examples of contemplated hybrid alpha-amylases include those disclosed in U.S. Publication no. 2005/0054071, including those disclosed in Table 3 on page 15, such as *Aspergillus niger* alpha-amylase with *Aspergillus kawachii* linker and starch binding domain.

Contemplated are also alpha-amylases which exhibit a high identity to any of above mention alpha-amylases, i.e., more than 70%, more than 75%, more than 80%, more than 85% more than 90%, more than 95%, more than 96%, more than 97%, more than 98%, more than 99% or even 100% identity to the mature enzyme sequences.

An acid alpha-amylases may according to the invention be added in an amount of 0.1 to 10 AFAU/g DS, preferably 0.10 to 5 AFAU/g DS, especially 0.3 to 2 AFAU/g DS.

Commercial Alpha-Amylase Products

Preferred commercial compositions comprising alpha-amylase include MYCOLASE from DSM, BAN™, TERMAMYL™ SC. FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ AA, and SPEZYME™ DELTA AA (Genencor Int.), and the acid fungal alpha-amylase sold under the trade name SP288 (available from Novozymes A/S, Denmark).

Carbohydrate-Source Generating Enzyme

The term "carbohydrate-source generating enzyme" includes glucoamylase (being glucose generators), beta-amylase and maltogenic amylase (being maltose generators). A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated mixtures are mixtures of at least a glucoamylase and an alpha-amylase, especially an acid amylase, even more preferred an acid fungal alpha-amylase. The ratio between acidic fungal alpha-amylase activity (AFAU) per glucoamylase activity (AGU) (AFAU per AGU) may in an embodiment of the invention be at least 0.1, in particular at least 0.16, such as in the range from 0.12 to 0.50 or more. Alternatively the ratio between acid fungal alpha-amylase activity (FAU-F) and glucoamylase activity (AGU) (i.e., FAU-F per AGU) may in an embodiment of the invention be between 0.1 and 100 AGU/FAU-F, in particular between 2 and 50 AGU/FAU-F, such as in the range from 10-40 AGU/FAU-F.

Glucoamylase

A glucoamylase used according to the invention may be derived from any suitable source, e.g. derived from a microorganism or a plant. Preferred glucoamylases are of fungal or bacterial origin, selected from the group consisting of *Aspergillus* glucoamylases, in particular *A. niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (*Agric. Biol. Chem.*, 1991, 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe at al., 1996, *Biochemistry* 35; 8698-8704; and introduction of Pro residues in position A435 and 6436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, "Purification and properties of the raw-starch-degrading glucoamylases from *Corticium rolfsii, Appl Microbiol Biotechnol* 50: 323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215).

Bacterial glucoamylases contemplated include glucoamylases from the genus *Clostridium*, in particular *C. thermoamylolyticum* (EP 135,138), and *C. thermohydrosulfuricum* (WO 86/01831) and *Trametes cingulata* disclosed in WO 2006/069289 (which is hereby incorporated by reference).

Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference.).

Contemplated are also glucoamylases which exhibit a high identity to any of above mention glucoamylases, i.e., more than 70%, more than 75%, more than 80%, more than 85% more than 90%, more than 95%, more than 96%, more than 97%, more than 98%, more than 99% or even 100% identity to the mature enzymes sequences.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ M PLUS (from DSM); G-ZYME™ M G900, G-ZYME™ M and G990 ZR (from Genencor Int.).

Glucoamylases may in an embodiment be added in an amount of 0.02-20 AGU/g DS, preferably 0.1-10 AGU/g DS, especially between 1-5 AGU/g DS, such as 0.5 AGU/g DS.

Beta-Amylase

At least according to the invention beta-amylase (E.C 3.2.1.2) is the name traditionally given to exo-acting maltogenic amylases, which catalyze the hydrolysis of 1,4-alpha-glucosidic linkages in amylase, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (Fogarty and Kelly, 1979. *Progress in Industrial Microbiology* 15: 112-115). These beta-amylases are characterized by having optimum temperatures in the range from 40° C. to 65° C. and optimum pH in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylase

The amylase may also be a maltogenic alpha-amylase. A "maltogenic alpha-amylase" (glucan 1,4-alpha-maltohydrolase, E.C. 3.2.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Proteases

The protease may according to the invention be any protease. In a preferred embodiment the protease is an acid protease of microbial origin, preferably of fungal or bacterial origin.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Cariolus, Endothia, Enthomophtra, Irpex, Penicillium, Sclerotiumand,* and *Torulopsis*. Especially contemplated are proteases derived from *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem.* 42(5): 927-933, *Aspergillus aculeatus* (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the proteases having at least 90% identity to amino acid sequence disclosed as SEQ ID NO: 13 such as at 92%, at least 95%, at least 96%, at least 97%, at least 98%, or particularly at least 99% identity.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

Proteases may be added in the amounts of 0, 1-1000 AU/kg dm, preferably 1-100 AU/kg DS and most preferably 5-25 AU/kg DS.

Use

In the third aspect the invention relates to the use of one or more phenolic compound oxidizing enzymes and/or enzymes exhibiting peroxidase activity for detoxifying pretreated lignocellulose-containing material.

In a preferably embodiment the phenolic compound oxidizing enzyme may be selected from the group comprising catechol oxidase (EC 1.10.3.1), laccase (EC 1.10.3.2), o-aminophenol oxidase (EC 1.10.3.4); and monophenol monooxygenase (EC 1.14.18.1) for detoxifying pre-treated lignocellulose-containing material.

In another preferred embodiment the enzyme exhibiting peroxidase activity may be selected from the group comprising peroxidase (EC 1.11.1.7), haloperoxidase (EC1.11.1.8 and EC 1.11.1.10); lignin peroxidase (EC 1.11.1.14); manganese peroxidase (EC 1.11.1.13); and lipoxygenase (EC. 1.13.11.12) for detoxifying pre-treated lignocellulose-containing material.

The detoxification may be part of a fermentation product production process of the invention.

Materials & Methods

Enzymes:

Laccase PpL: Laccase derived from *Polyporus pinsitus* disclosed in WO 1996/000290 (Novozymes).

Laccase MtL: Laccase derived from *Myceliopthora thermophila* disclosed in WO 1995/033836 (Novozymes).

Laccase CCL: Laccase derived from *Coprinus cinereus* disclosed in WO 97/08325 (Novozymes)

Peroxidase CcP: Peroxidase is derived from *Coprinus cinereus* disclosed in Petersen et al., 1994. *FEBS Letters* 339: 291-296.

Cellulolutic preparation A: Cellulolytic composition comprising a polypeptide having cellulalytic enhancing activity (GH61A) disclosed in WO 2005/074656; a beta-glucosidase (fusion protein disclosed in U.S. provisional application No. 60/832,511), *Thielavia terrestris* cellobiohydrolase II (CEL6A), and cellulolytic enzymes preparation derived from *Trichoderma reesei*. Cellulase preparation A is disclosed in U.S. provisional application No. 60/941,251.

Cellulolytic preparation B: Cellulolytic composition comprising a polypeptide having cellulolytic enhancing activity (GH61A) disclosed in WO 2005/074656; a beta-glucosidase (fusion protein disclosed in U.S. provisional application No. 60/832,511); and cellulolytic enzymes preparation derived from *Trichoderma reesei*. Cellulase preparation A is disclosed in U.S. provisional application No. 60/941,251.

Yeast: RED STAR™ available from Red Star/Lesaffre, USA

Pre-treated corn stover: dilute acid-catalyzed steam explosion corn stover (28.6% DS) was obtained from NREL (National Renewable Research Laboratory, USA).

Determination of Identity

The relatedness between two amino acid sequences or between two nucleotide sequences is described by the parameter "Identity".

The degree of identity between two amino acid sequences may be determined by the Clustal method (Higgins, 1989, *CABIOS* 5: 151-153) using the LASEGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

The degree of identity between two nucleotide sequences may be determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10, Pairwise alignment parameters are Ktuple=3, gap penalty=3; and windows=20.

Determination of Laccase Activity (LACU)

Laccase activity is determined from the oxidation of syringaldazin under aerobic conditions. The violet color produced is photometered at 530 nm. The analytical conditions are 19 mM syringaldazin, 23.2 mM acetate buffer, pH 5.5, 30° C., 1 min. reaction time.

1 laccase unit (LACU) is the amount of enzyme that catalyzes the conversion of 1.0 micromole syringaldazin per minute at these conditions.

Determination of Peroxidase Activity (PODU)

One peroxidase unit (PODU) is defined as the amount of enzyme which, under standard conditions (i.e., pH 7.0; temperature 30° C.; reaction time 3 minutes) catalyzes the conversion of 1 micromole hydrogen peroxide per minute. The activity is determined using an assay based on ABTS® (2,2'-azinobis(3-ethylbenzothiazoline-6-sulfonate)) as the chromophore, the greenish-blue colour produced being photometered at 418 nm. A folder AF 279/2 describing this analytical method in more detail is available upon request to Novozymes A/S, Denmark, which folder is hereby included by reference.

Glucoamylase Activity

Glucoamylase activity may be measured in Glucoamylase Units (AGU).

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$, and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-amylase Activity

When used according to the present invention the activity of an acid alpha-amylase may be measured in AFAU (Acid Fungal Alpha-amylase Units) or FAU-F (Fungal Alpha-Amylase Units).

Acid Alpha-amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch, Amylase activity is determined using reverse colorimetry as a reduction in the concentration of starch under the specified analytical conditions.

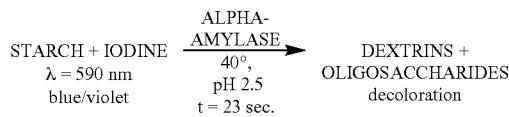

Standard Conditions/Reaction Conditions:

| Substrate: | Soluble starch, approx. 0.17 g/L |
|---|---|
| Buffer: | Citrate, approx. 0.03 M |
| Iodine (I2): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Measurement of Cellulase Activity Using Filter Paper Assay (FPU Assay)

1. Source of Method 1.1 The method is disclosed in a document entitled "Measurement of Cellulase Activities" by Adney and Baker, 1996, Laboratory Analytical Procedure, LAP-006, National Renewable Energy Laboratory (NREL). It is based on the IUPAC method for measuring cellulase activity (Ghose, 1987, Measurement of Cellulase Activities. *Pure & Appl. Chem.* 59: 257-268.

2. Procedure 2.1 The method is carried out as described by Adney and Baker, 1996, supra, except for the use of a 96 well plates to read the absorbance values after color development, as described below.

2.2 Enzyme Assay Tubes:

2.2.1 A rolled filter paper strip (#1 Whatman; 1×6 cm; 50 mg) is added to the bottom of a test tube (13×100 mm).

2.2.2 To the tube is added 1.0 mL of 0.05 M Na-citrate buffer (pH 4.80).

2.2.3 The tubes containing filter paper and buffer are incubated 5 min. at 50° C. (±0.1° C.) in a circulating water bath.

2.2.4 Following incubation, 0.5 mL of enzyme dilution in citrate buffer is added to the tube. Enzyme dilutions are designed to produce values slightly above and below the target value of 2.0 mg glucose.

2.2.5 The tube contents are mixed by gently vortexing for 3 seconds.

2.2.6 After vortexing, the tubes are incubated for 60 mins. at 50° C. (±0.1° C.) in a circulating water bath.

2.2.7 Immediately following the 60 min. incubation, the tubes are removed from the water bath, and 3.0 mL of DNS reagent is added to each tube to stop the reaction. The tubes are vortexed 3 seconds to mix.

2.3 Blank and Controls 2.3.1 A reagent blank is prepared by adding 1.5 mL of citrate buffer to a test tube.

2.3.2 A substrate control is prepared by placing a rolled filter paper strip into the bottom of a test tube, and adding 1.5 mL of citrate buffer.

2.3.3 Enzyme controls are prepared for each enzyme dilution by mixing 1.0 mL of citrate buffer with 0.5 mL of the appropriate enzyme dilution.

2.3.4 The reagent blank, substrate control, and enzyme controls are assayed in the same manner as the enzyme assay tubes, and done along with them.

2.4 Glucose Standards 2.4.1 A 100 mL stock solution of glucose (10.0 mg/mL) is prepared, and 5 mL aliquots are frozen. Prior to use, aliquots are thawed and vortexed to mix.

2.4.2 Dilutions of the stock solution are made in citrate buffer as follows:

G1=1.0 mL stock+0.5 mL buffer=6.7 mg/mL=3.3 mg/0.5 mL

G2=0.75 mL stock+0.75 mL buffer=5.0 mg/mL=2.5 mg/0.5 mL

G3=0.5 mL stock+1.0 mL buffer=3.3 mg/mL=1.7 mg/0.5 mL

G4=0.2 mL stock+0.8 mL buffer=2.0 mg/mL=1.0 mg/0.5 mL 2.4.3 Glucose standard tubes are prepared by adding 0.5 mL of each dilution to 1.0 mL of citrate buffer.
2.4.4 The glucose standard tubes are assayed in the same manner as the enzyme assay tubes, and done along with them,
2.5 Color Development
2.5.1 Following the 60 min, incubation and addition of DNS, the tubes are all boiled together for 5 mins, in a water bath.
2.5.2 After boiling, they are immediately cooled in an ice/water bath.
2.5.3 When cool, the tubes are briefly vortexed, and the pulp is allowed to settle. Then each tube is diluted by adding 50 microL from the tube to 200 microL of $ddH_2O$ in a 96-well plate. Each well is mixed, and the absorbance is read at 540 nm.
2.6 Calculations (examples are given in the NREL document)
2.6.1 A glucose standard curve is prepared by graphing glucose concentration (mg/0.5 mL) for the four standards (G1-G4) vs. $A_{540}$. This is fitted using a linear regression (Prism Software), and the equation for the line is used to determine the glucose produced for each of the enzyme assay tubes.
2.6.2 A plot of glucose produced (mg/0.5 mL) vs. total enzyme dilution is prepared, with the Y-axis (enzyme dilution) being on a log scale.
2.6.3 A line is drawn between the enzyme dilution that produced just above 2.0 mg glucose and the dilution that produced just below that. From this line, it is determined the enzyme dilution that would have produced exactly 2.0 mg of glucose.
2.6.4 The Filter Paper Units/mL (FPU/mL) are calculated as follows:
FPU/mL 0.37/enzyme dilution producing 2.0 mg glucose
Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e., 25° C., pH 5.5 and 10 min. reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

EXAMPLES

Example 1

Effect of Laccase on Ethanol Yield During Enzymatic Hydrolysis

Dilute acid-catalyzed steam exploded pre-treated corn stover was obtained from NREL. The pre-treated corn stover (15% DS) was hydrolyzed at pH 4.5, 50° C. for 75 hours with Cellulolytic preparation A (5 FPU/g DS) with and without Laccase PpL (20-30 LACU/g DS). The enzymatic treatment was carried out with open lid so that consistent air flow was provided during the treatment. Evaporation was control by daily water supplement based on weight loss. The enzyme treated samples were used for ethanol fermentation at 32° C. for up to 88 hours in a closed vessel where a needle was punched in the cap, with yeast (RED STAR™) at initial dosage of 0.2 g/L. The fermentation mixture also contains YPU (5 g/L yeast extract, 5 g/L peptone and 10 g/L Urea). After 25 hours fermentation, the laccase treated sample resulted in 10 g/L ethanol production, whereas the non-laccase treated sample resulted in no ethanol yield. With initial yeast dosage of 1.6 g/L, about 10-fold higher ethanol production was observed with laccase treated sample after 25 hours fermentation (18.87 g/L for laccase treated samples vs 1.83 for non-laccase treated sample).

Example 2

Effect of Laccase on Ethanol Yield During Fermentation

The pre-treated corn stover (28.6% DS) used was the same as in Example 1. The pre-treated corn stover (15% DS) was hydrolyzed with Cellulolytic preparation A (5 FPU/g DS) at pH 4.5, 50° C. for 75 hours in the absence of laccase with covered lid. After the enzymatic hydrolysis, material was fermented at 32° C. for up to 88 hours in a closed vessel where a needle was punched in the cap, with yeast (RED STAR™) at dosage of 1.6 g/L with and without laccase PpL (20-30 LACU/g DS). The fermentation mixture also contains YPU (5 g/L yeast extract, 5 g/L peptone and 10 g/L Urea). After 25 hours, the ethanol production was doubled in the sample where laccase was present during fermentation (4.59 g/L laccase treated vs 1.83 non-laccase treated).

Example 3

Effect of Oxidoreductases Treatment in Between Hydrolysis and Yeast Fermentation The pre-treated corn stover (28.6% DS) used was the same as in Example 1, Enzymatic hydrolysis was carried out with pre-treated corn stover (15% DS) at pH 4.5, 50° C. for 72 hours in the absence of laccase with covered lid. Oxidoreductase treatment was conducted at 50° C. for one or two hours before fermentation at 32° C. (up to 48 hours) with yeast (RED STAR™) at dosage of 0.5 g/L in a closed vessel where a needle was punched in the cap. During oxidoreductase treatment, lids were opened every 20 minutes. The fermentation mixture also contains YPU (5 g/L yeast extract, 5 g/l peptone and 10 g/L Urea). Up to 40% increase in ethanol production was observed with Laccase PpL (4, 5-30 LACU/g DS). Up to 27% increase in ethanol production was observed with Laccase MtL (0.5-30 LACU/g DS). About 27% increase in ethanol production was observed with Laccase CcL (36 LACU/g DS). About 40% increase in ethanol production was observed with peroxidase CcP in the presence of 5% $H_2O_2$.

Example 4

Laccase-Mediated Improvement of PCS Enzymatic Hydrolysis
Collection of Pretreatment Liquor:

Liquor was collected from both neutral, steam exploded corn stover and from acid, steam exploded corn stover. Each PCS was slurried in deionized water to a final total solids (TS) level of 15 wt. % with mixing at ambient temperature for 1 hour. Each slurry was stored at CC for 16-20 hours. Slurries were then mixed at ambient temperature for 1 hour, and liquor was collected by vacuum filtration through a glass fiber filter (Whatman GF/D). Sodium azide was added to a final concentration of 0.02% w/w. The pH of each was adjusted to 5.0. After mixing for 1 hour at ambient temperature, liquor was vacuum filtered through a 0.2 micro m membrane and stored at 4° C.

Laccase Treatment:

All PCS liquors were adjusted to pH 5.0. Laccase MtL was dosed into PCS liquor to a final concentration of 100 ppm. The liquor containing laccase was incubated alongside a negative control liquor for 18 hours at 50° C. with 150 rpm of agitation. Any precipitated material was removed by centrifugation at 3000 rpm for 10 minutes prior to further characterization.

Folin-Ciocalteu (FC) Method for Phenolics:

The method was modified from a published procedure (Singleton, Orthofer, and Lamuela-Raventos, 1999, *Methods Enzymol.* 299: 152-178). Catechol (Sigma #135011) calibration standards and sample dilutions were prepared in deionized water. Fifty microL of diluted sample or catechol calibration standard were transferred to the wells of a microliter plate. Deionized water (50 microL) was added to each well followed by 50 microL/well of FC reagent (Sigma #F9252). The plate was incubated for 5 minutes at ambient temperature. Sodium carbonate (15% w/v, 100 microL) was then added to each well and the plate was incubated for 30 minutes at ambient temperature in the dark. The absorbance at 770 nm of each well was collected. Unknown total phenolic concentrations were calculated from the catechol standard curve by linear regression analysis in Microsoft Excel.

PCS Hydrolysis and Glucose Monitoring.

Washed PCS solids were slurried in the appropriate PCS liquor at a final concentration of 4% total solids and dosed with Cellulolytic preparation B (3 mg protein/g cellulose). Hydrolysis reactions were incubated at 50° C. with shaking (150 rpm) for 48 hours. Glucose concentrations were monitored over time using an enzyme-coupled glucose assay.

TABLE 1

Effect of laccase treatment on soluble phenolics as measured by FC method

| Liquor | Phenolics, mg/mL | | % Decrease |
|---|---|---|---|
| | −laccase | +laccase | |
| Neutral PCS | 2.30 ± 0.05 | 1.63 ± 0.01 | 29.1 |
| Acid PCS | 1.96 ± 0.02 | 1.34 ± 0.02 | 31.8 |

CONCLUSIONS

Enzymatic hydrolysis of PCS was improved by treating PCS liquor with a laccase. Laccase treatment of either neutral or acid PCS liquors resulted in an 8-10% improvement in cellulose conversion.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fail within the scope of the appended claims. In the case of conflict, the present disclosure, including definitions will be controlling.

Various references are cited herein, the disclosures of which are incorporated by reference in their entireties.

The invention claimed is:

1. A process for producing a fermentation product, comprising:
   (a) pre-treating a lignocellulose-containing corn stover or corn fiber material that contains between 30-60 wt. % lignocellulose, with dilute-acid catalyzed steam explosion, to produce a pre-treated lignocellulose-containing material;
   (b) separating said pre-treated material of step (a), into a liquor fraction and solids fraction after pre-treating and then detoxifying the separated liquor fraction, unwashed, with a phenolic compound oxidizing enzyme a laccase (EC 1.10.3.2), to produce a detoxified material;
   (c) after step (b), hydrolyzing the detoxified material with a cellulolytic enzyme preparation comprising a cellulase and a polypeptide having cellulolytic enhancing activity that is a family GH61A polypeptide, to produce a sugar;
   (d) fermenting the sugar in a fermentation medium/broth using a fermenting yeast, to produce a fermentation product comprising an alcohol; and
   (e) separating the alcohol of step (d) from the fermentation medium/broth.

2. The process of claim 1, wherein the hydrolysis step (c) and the fermentation step (d), are carried out as a simultaneous saccharification and fermentation.

3. The process of claim 1, wherein the fermentation product is ethanol.

4. The process of claim 1, wherein the cellulolytic enzyme preparation is derived from *Trichoderma reesei*.

5. The process of claim 1, wherein the hydrolysis step (c) and the fermentation step (d), are carried out as a hybrid hydrolysis and fermentation.

* * * * *

UNITED STATES PATENT AND TRADEMARK OFFICE
CERTIFICATE OF CORRECTION

PATENT NO. : 10,023,881 B2  
APPLICATION NO. : 12/597834  
DATED : July 17, 2018  
INVENTOR(S) : Jin et al.

Page 1 of 1

It is certified that error appears in the above-identified patent and that said Letters Patent is hereby corrected as shown below:

In the Specification

At Column 1, Line 15, please add the following:
STATEMENT AS TO RIGHTS TO INVENTIONS MADE UNDER FEDERALLY SPONSORED RESEARCH AND DEVELOPMENT
This invention was made with government support under Cooperative Agreement No. 04-03-CA-70759 awarded by the Department of Energy. The Government has certain rights in the invention.

Signed and Sealed this  
Eighteenth Day of June, 2019

Andrei Iancu  
*Director of the United States Patent and Trademark Office*